United States Patent [19]
Jones et al.

[11] Patent Number: 4,859,512
[45] Date of Patent: Aug. 22, 1989

[54] TRANSFER ADHESIVE SANDWICH FOR APPLYING ADHESIVE TO SUBSTRATES

[75] Inventors: Wallace R. Jones, Waite Hill Village; Robert A. Isaksen, Chardon; Paul A. Krieger, North Ridgeville, all of Ohio

[73] Assignee: The Excello Specialty Company, Cleveland, Ohio

[21] Appl. No.: 162,110

[22] Filed: Feb. 29, 1988

Related U.S. Application Data

[63] Continuation of Ser. No. 892,472, Aug. 1, 1986, Pat. No. 4,728,380.

[51] Int. Cl.$^4$ .................. A61F 13/02; E04F 15/16; B32B 31/00
[52] U.S. Cl. ..................... 428/40; 428/352; 428/202; 156/230; 156/249; 156/289
[58] Field of Search ............. 428/40, 41, 42, 132, 428/134, 135, 202, 261, 200, 198, 352, 914, 213; 156/230, 240, 235, 246, 248, 249, 289, 344; 40/158 B, 594, 152; 283/101, 112, 900; 427/208.8, 207.1, 256; 200/5 A

[56] References Cited

U.S. PATENT DOCUMENTS

| | | | |
|---|---|---|---|
| 2,914,167 | 11/1959 | Holtz | 427/208.8 |
| 3,626,618 | 12/1971 | Tone et al. | 40/158 B |
| 3,741,786 | 6/1973 | Torrey | 428/202 |
| 3,853,576 | 12/1974 | Netzuik | 156/247 |
| 3,869,333 | 3/1975 | McMaster | 428/138 |
| 3,886,012 | 5/1975 | Slater | 156/289 |
| 4,028,474 | 6/1977 | Martin | 428/202 |
| 4,041,200 | 8/1977 | Boraniau et al. | 428/352 |
| 4,055,454 | 10/1977 | Laske | 428/198 |
| 4,113,906 | 9/1978 | Brandwein | 428/42 |
| 4,258,096 | 3/1981 | LaMarche | 200/5 A |
| 4,303,811 | 12/1981 | Parkinson | 200/5 A |
| 4,331,727 | 5/1982 | Maas | 428/213 |
| 4,333,258 | 6/1982 | Stevenson | 40/158 B |
| 4,373,122 | 2/1983 | Frame | 200/5 A |
| 4,380,563 | 4/1983 | Agotte | 428/40 |
| 4,588,627 | 5/1986 | Isaksen et al. | 428/352 |
| 4,642,925 | 2/1987 | Thompson | 428/134 |
| 4,654,250 | 3/1987 | Black et al. | 428/352 |

FOREIGN PATENT DOCUMENTS 0042125 12/1981 European Pat. Off. ......... 40/158 B

Primary Examiner—Michael W. Ball
Assistant Examiner—Louis Falasco
Attorney, Agent, or Firm—Fay, Sharpe, Beall, Fagan, Minnich & McKee

[57] ABSTRACT

A transfer adhesive sandwich includes a flexible carrier sheet having an adhesive layer releasably bonded to one surface and having an opposite surface to which the adhesive layer is releasably bondable with substantially less tenacity than the tenacity of the bond between the adhesive layer and the one surface. A plurality of the sandwiches are stacked on top of one another to form a pad from which individual sandwiches are strippable. When the adhesive layer is pressed against a substrate, it adheres to the substrate with a tenacity substantially greater than the tenacity of the bond between the adhesive layer and the one surface of the carrier sheet so that the carrier sheet can be stripped away to leave the adhesive layer on the substrate.

3 Claims, 2 Drawing Sheets

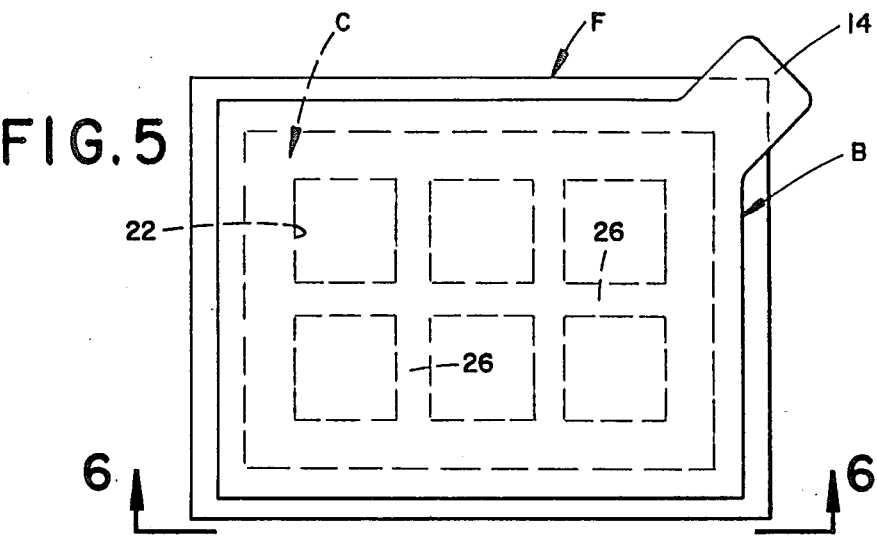
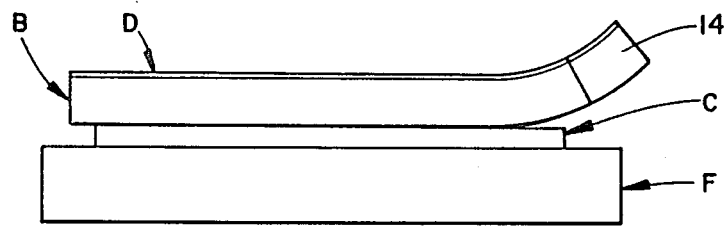
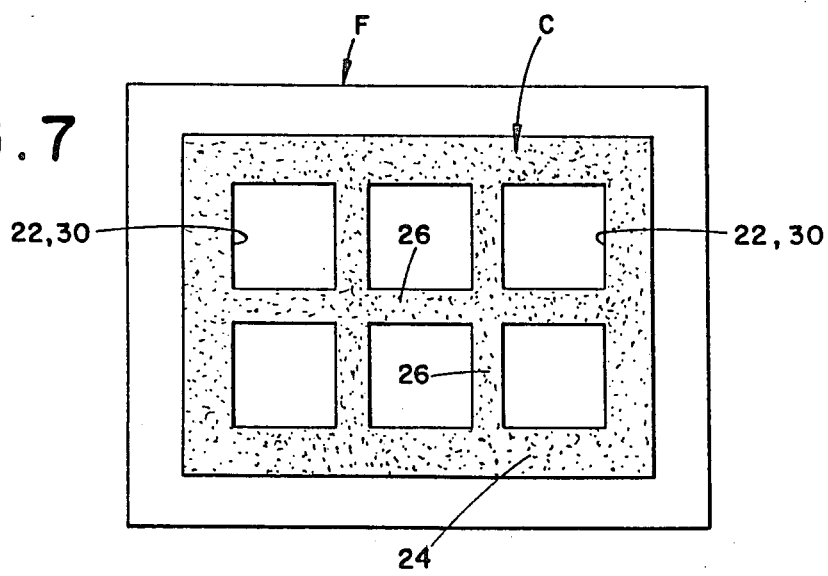

TRANSFER ADHESIVE SANDWICH FOR APPLYING ADHESIVE TO SUBSTRATES

This is a continuation, of application Ser. No. 892,472, filed Aug. 1, 1986, now U.S. Pat. No. 4,728,380.

BACKGROUND OF THE INVENTION

This invention relates to the art adhesive laminates and to a method of applying adhesive to a substrate. The laminate and method of the present invention are particularly adapted for use in attaching a substrate framework to another member and will be described with specific reference thereto. However, it will be appreciated that the invention has broader aspects and may be used for other purposes in many different environments.

Many devices are operated by electronic controls having manually operable membrane or push-button switches which are accessible through openings in a substrate framework or face plate attached to the device. It is common to attach the framework or face plate with the use of adhesive which is applied to the rear surface of the framework or face plate. Properly applying adhesive to the rear surface of the framework requires care so that the appearance of the device will not be marred and so that the framework will be securely attached against accidental displacement. It would be desirable to have a simple and clean arrangement for applying adhesive to frameworks of the type described.

SUMMARY OF THE INVENTION

A transfer adhesive sandwich includes a flexible carrier sheet having a layer of pressure-sensitive adhesive releasably bonded to one surface thereof and having an opposite surface to which the adhesive layer is bondable with a tenacity substantially weaker than the tenacity of the bond between the adhesive layer and the one surface. A plurality of the sandwiches are stacked on top of one another to form a pad, with the adhesive layer on each sandwich engaging the opposite surface of a carrier sheet on an adjacent sandwich. The sandwiches are strippable one by one from the pad.

In accordance with the present invention, the adhesive layer on a sandwich is pressed into engagement with a substrate to which the adhesive layer bonds with a tenacity substantially greater than the tenacity of the bond between the adhesive layer and the one surface of the carrier sheet. Pulling on the carrier sheet then strips the sheet from the adhesive layer such that the adhesive layer remains bonded to the substrate. The substrate can then be attached to or receive another device or base member through the use of the pressure-sensitive adhesive layer.

The carrier sheet may comprise polyethylene or other suitable flexible materials. The opposite surface of the carrier sheet may be provided with a release material so that the adhesive layer of one sandwich will adhere very lightly to the opposite surface of a carrier sheet on an adjacent sandwich for maintaining the integrity of the pad while allowing easy stripping of individual sandwiches from the pad. Where the carrier sheet is a material to which the adhesive layer does not readily adhere, it may be unnecessary to provide a layer of release material on the opposite surface thereof. In such a situation, the one surface of the carrier sheet may be suitably treated for enhancing the bond between the adhesive layer and the one surface. Thus, the opposite surfaces of the carrier sheet have characteristics such that the adhesive layer bonds to one surface with a tenacity substantially greater than the tenacity to which it bonds to the opposite surface.

The carrier sheet preferably includes an outwardly extending tab which is not coated with adhesive so that it can be readily grasped for pulling a sandwich from the pad, and for pulling a carrier sheet away from the adhesive layer bonded to a substrate.

The adhesive layer is preferably applied to a carrier sheet in a discontinuous pattern having a plurality of spaced-apart openings therein surrounded by adhesive. The openings in the adhesive layer correspond in size, shape, and spacing with openings through a substrate framework or face plate to be applied to a device having manually operable membrane or push-button switches aligned with the openings.

One principal advantage of the present invention is the provision of a new transfer adhesive sandwich.

Another principal advantage of the invention resides in the provision of a new method for applying pressure sensitive adhesive to substrates.

A further advantage of the invention is the provision of a transfer adhesive sandwich and method which make it very simple and economical to apply adhesive to substrate frameworks or the like.

Still other advantages and benefits of the invention will be come apparent to those skilled in the art upon a reading and understanding of the following detailed description.

BRIEF DESCRIPTION OF THE DRAWINGS

The invention may take form in certain parts and arrangements of parts, a preferred embodiment of which will be described in detail in this specification and illustrated in the accompanying drawings which form a part hereof and wherein:

FIG. 5 is a view similar to FIG. 4 showing the sandwich of FIGS. 1 and 2 positioned in engagement with the rear surface of the substrate framework;

FIG. 6 is an end elevational view taken generally in the direction of lines 6—6 of FIG. 5 and showing a carrier sheet being stripped from its adhesive layer; and, FIG. 7 is a rear plan view of the substrate framework of FIG. 4 with a layer of adhesive applied thereto following the procedures of FIGS. 5 and 6.

DETAILED DESCRIPTION OF THE PREFERRED EMBODIMENT

Figure 1:
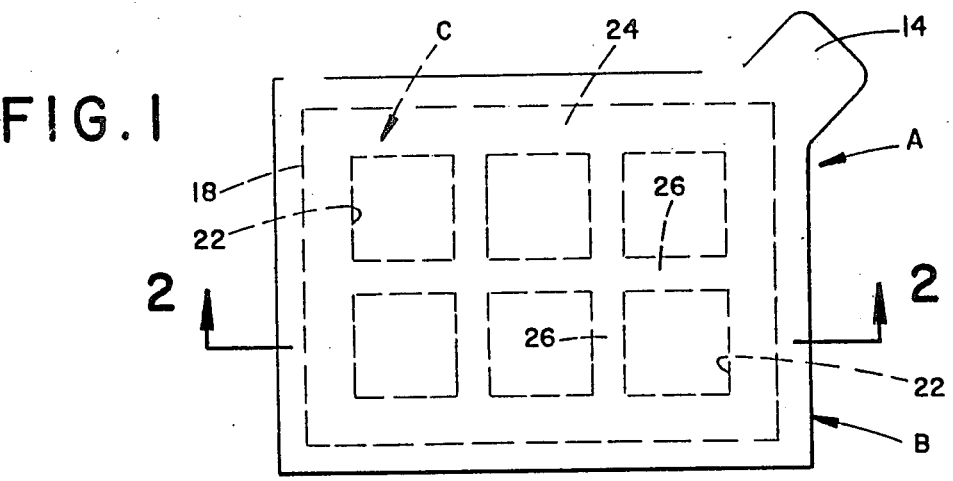
FIG. 1 is a top plan view of a transfer adhesive sandwich constructed in accordance with the present invention.
Figure 2:
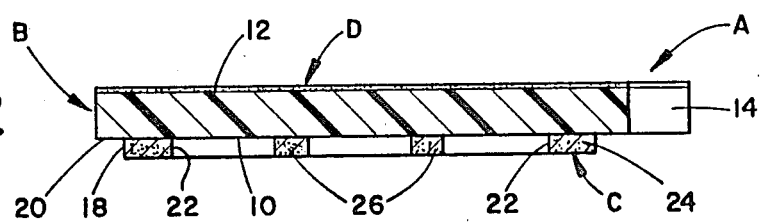
FIG. 2 is a cross-sectional elevational view taken generally along lines 2—2 of FIG. 1.

Referring now to the drawings wherein the showings are for purposes of illustrating a preferred embodiment of the invention only and not for purposes of limiting same, FIG. 1 shows a transfer adhesive sandwich A constructed in accordance with the present invention and including a flexible carrier sheet B having opposite planar surfaces 10, 12 (FIG. 2).

A layer C of pressure-sensitive adhesive is releasably bonded to one surface 10 of carrier sheet B. Opposite surface 12 of the carrier sheet has a layer of release material D thereon and to which adhesive layer C is releasably bondable with a tenacity substantially weaker than the tenacity of the bond between adhesive layer C and one surface 10.

At least one tab 14 projects outwardly from carrier sheet B to be grasped for pulling on carrier sheet B and otherwise manipulating same. Tab 14 is completely free of any adhesive. Where carrier sheet B is generally rectangular in the manner shown in the FIGURES, tab 14 projects generally diagonally outward from one corner thereof and is of a size to accommodate easy grasping between a person's thumb and index finger. The intersections of the edges of tab 14 with the edges of carrier sheet B are preferably smoothly curved as shown in FIG. 1 to avoid stress concentrations. This, in turn, prevents tearing of carrier sheet B when tab 14 is pulled to separate a sandwich from a pad, or to seaprate a carrier sheet from its adhesive layer.

Pressure-sensitive adhesive layer C is applied to one surface 10 of carrier sheet B in a predetermined discontinuous pattern. Adhesive layer C has a continuous outer periphery 18 which is spaced inwardly from the outer periphery of carrier sheet B to leave a peripheral border 20 on one surface 10 which is free of adhesive. In the arrangement shown, the discontinuous pattern of pressure-sensitive adhesive layer C is such that a plurality of spaced-apart openings 22 are provided therein. As shown, openings 22 are generally square, and it will be recognized that other shapes and patterns can be used to accommodate different applications or installations without in any way departing from the overall intent or scope of the invention. Also, although six openings 22 are shown in FIG. 1, it will be recognized that a greater or lesser number of such openings can be provided, and that the openings can have irregular spacings.

Openings 22 in adhesive layer C are completely surrounded by adhesive, and adhesive layer C has an outer border 24 which is substantially wider than adhesive webs 26 between adjacent openings 22. In the arrangement shown, adhesive outer border 24 generally corresponds with the shape of border 20 on one surface 10 of carrier sheet B. However, it will be recognized that the peripheral shape of adhesive layer C may differ from that of carrier sheet B. When sandwich A is used for attaching a substrate framework to a device having membrane or push-button switches, openings 22 are generally equidistantly spaced both horizontally and vertically.

It will be recognized that many different materials can be used for flexible carrier sheet B. In one arrangement, polyethylene plastic film has been used with excellent results. However, it will be recognized by those skilled in the art that other materials compatible with the particular adhesive and the particular application can be satisfactorily employed. When polyethylene has been used, the thickness of carrier sheet B is approximately six mils, while the thickness of pressure-sensitive adhesive layer C is approximately one mil and the thickness of release layer D, if provided, is approximately one-half mil. In general, the thickness of carrier sheet B will be substantially greater than that of adhesive layer C which, in turn, will be substantially greater than the thickness of release layer D. However, the degree by which the thickness of flexible carrier sheet B exceeds the thickness of adhesive layer C will normally be many times that by which the thickness of adhesive layer C exceeds that of release layer D.

For certain materials and adhesives, it may be possible to omit release layer D as would be the case when carrier sheet B has surface characteristics such that pressure-sensitive adhesive layer C will bond only lightly to carrier sheet opposite surface 12. Under these circumstances, it may be desirable to treat carrier sheet one surface 10 prior to application of adhesive layer C thereto so that such layer will bond to one surface 10 with a tenacity substantially greater than it will bond to opposite surface 12. However, if adhesive layer C is hot when applied to one surface 10, it may bond thereto with a tenacity substantially greater than it will bond to opposite surface 12 when cold, and no treatment of either surface may be necessary. In any event, the sandwich is characterized by a carrier sheet having one surface to which a pressure-sensitive adhesive layer is bonded with a tenacity substantially greater than the tenacity with which such adhesive layer is bondable to the opposite surface thereof. Although adhesive layer C has openings 22 therein, it will be recognized and appreciated that, preferably, carrier sheet B is continuous.

Figure 3:
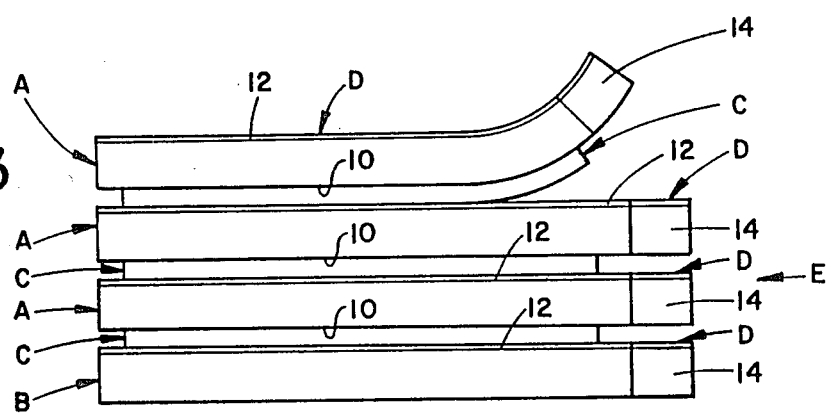
FIG. 3 is a side elevational view showing a plurality of the sandwiches of FIGS. 1 and 2 stacked on top of one another.

FIG. 3 shows a pad E formed by a plurality of sandwiches A stacked in alignment on top of one another. For ease of illustration, FIG. 3 shows only a few sandwiches A on an enlarged scale, and pad E normally will be comprised of around twenty-five or more of these sandwiches. However, it is to be recognized that any number of sandwiches A could be included in a pad as may be necessary and/or desired. Sandwiches A are stacked on top of one another with the adhesive layer C on one sandwich engaging and being releasably bonded to release layer or material D on the adjacent sandwich. Thus, the top sandwich A is strippable from the pad by grasping tab 14 and pulling same as indicated in FIG. 3. In view of the fact that the tenacity of the bond between surface 10 of a carrier sheet B and adhesive layer C is substantially greater than the tenacity of the bond between adhesive layer C and release layer D, an entire sandwich as described with respect to FIGS. 1 and 2 is strippable from pad E of FIG. 3. At the same time, there is aome adhesion between pressure-sensitive adhesive layer C and release layer D for maintaining the alignment and integrity of pad E. The bottom carrier sheet B in pad E will not have an adhesive layer C applied thereto. In the alternative, it is possible to simply place a layer of release material or paper over adhesive layer C of the bottom sandwich.

Figure 4:
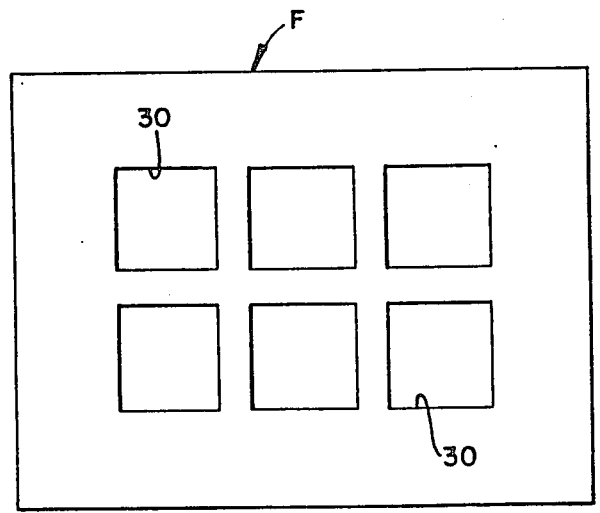
FIG. 4 is a rear plan view of a substrate framework having a plurality of openings therein alignable with membrane or push-button sandwiches.

FIG. 4 shows a substrate framework or face plate F having a plurality of spaced-apart openings 30 therethrough generally corresponding in size, shape, and spacing to openings 22 in adhesive layer C on a sandwich B. Openings 22 in the adhesive layer are preferably somewhat larger in size than openings 30 so that alignment of adhesive layer C with the rear surface of the substrate framework is not critical. Substrate framework F may be comprised of any suitable material such as metal, plastic, wood, paper or such which are painted or otherwise coated. The substrate framework will normally have a thickness which is substantially greater than the thickness of carrier sheet B and will be substantially rigid as compared to the carrier sheet.

The surface characteristics of at least the rear surface of substrate framework F are also such that pressure-sensitive adhesive layer C will adhere thereto with a tenacity substantially greater than the tenacity of the bond between adhesive layer C and one surface 10 of a carrier sheet B. As previously explained, openings 22 in adhesive layer C are preferably somewhat larger than openings 30 in substrate framework F and adhesive webs 26 of adhesive layer C are also substantially narrower than the width of the webs between adjacent openings 30. Such an arrangement makes it possible to rapidly position a sandwich B on the rear surface of substrate framework F with adhesive layer openings 22 generally aligned with openings 30 and without having any adhesive projecting into openings 30. At the same time, the adhesive layer will completely surround each opening 30 in the substrate framework.

FIG. 5 shows a sandwich B after it has been stripped from pad E of FIG. 3 and is being applied to the rear surface of a substrate framework F of FIG. 4. Sandwich B is positioned with its pressure-sensitive adhesive layer C engaging the rear surface of the substrate framework and with openings 22 in adhesive layer C generally aligned with openings 30 in substrate framework F.

Once carrier sheet B is pressed against the rear surface of substrate framework F, tab 14 is grasped and pulled away from the substrate framwork in order to pull the flexible carrier sheet away from adhesive layer C. The adhesive layer, in turn, remains bonded to substrate framework F as shown in FIG. 6. Once carrier sheet B is pulled completely away from adhesive layer C, the rear surface of substrate framework F appears as shown in FIG. 7 with adhesive layer C bonded thereto in surrounding relationship to openings 30. Substrate F may then be applied to another device or base member so that membrane or push-button switches are aligned with openings 30. The device or base member to which substrate framework F is applied may be of any known type such as a kitchen appliance in the form of a range or oven having membrane or push-button switches to operate an electronic control. The substrate framwork may also be applied to various industrial control boxes, or to electronic calculators or the like.

In the subject invention, assembly of a plurality of sandwiches into a pad prevents drying of the pressure-sensitive adhesive layer C until it is ready for use by stripping a sandwich from the pad. Also, the pad eliminates the need for a separate release paper or the like on the exposed surface of each adhesive layer. In one form of the invention, the carrier sheet and the release layer (if required) are generally transparent to accommodate ready alignement of the adhesive pattern with the substrate pattern. Also, the adhesive is generally opaque so that the adhesive pattern may be clearly differentiated from the carrier sheet. It is to be appreciated, however, that other arrangements could also be satisfactorily employed to facilitate ease of alignment. For example, the carrier sheets may include printed indicia or the like which are alignable with a selected area of an associated substrate so that, in turn, the adhesive pattern will be properly aligned with the substrate pattern.

The specific chemical conformation of the adhesive material does not itself comprise a part of the present invention. However, depending upon the intended application for the subject new transfer adhesive sandwich, it may be desirable to have the adhesive include certain physical and/or chemical characteristics. For example, the ability of the adhesive to conduct static electricity would be advantageous when the adhesive sandwich is to be used in association with membrane-type switch plates or the like. Also, a water-soluble adhesive would be advantageous for accommodating soldering or the like. Still other capabilities for or characteristics of the adhesive material would be desirable as a function of the specific use intended for the sandwiches.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is now claimed:

1. A pad of adhesive sandwiches stacked on top of one another and intended for applying adhesive to substrates having a plurality of spaced apart openings therein, each sandwich including a flexible carrier sheet having a pressure-sensitive adhesive layer releasably bonded to one surface thereof, said sheet having an opposite surface to which said adhesive layer is releasably bondable with a tenacity substantially less than the tenacity of the bond between said adhesive layer and said one surface, said sandwiches being stacked with said adhesive layer on one carrier sheet engaging said opposite surface of an adjacent carrier sheet, whereby said sandwiches are strippable from said pad one by one for engaging the adhesive layer with a substrate to which the adhesive layer is bondable with a tenacity substantially greater than the tenacity of the bond between the adhesive layer and carrier sheet so that the carrier sheet is strippable from the adhesive layer which remains on the substrate said adhesive layer having a predetermined discontinuous pattern with a plurality of spaced apart openings constituting areas of said carrier sheet to which adhesive has not been applied and corresponding in size and shape to the spaced apart openings in said substrate.

2. The pad as defined in claim 1 wherein said opposite surface of each carrier sheet has a release material thereon.

3. The pad as defined in claim 1 wherein each carrier sheet has at least one tab extending outwardly thereof and being free of adhesive, said tab being graspable to facilitate stripping of sandwiches from the pad and of a carrier sheet from its adhesive layer.

* * * * *